(12) United States Patent
Martin et al.

(10) Patent No.: US 6,475,728 B1
(45) Date of Patent: Nov. 5, 2002

(54) METHOD FOR IDENTIFYING AND/OR ANALYZING BIOLOGICAL SUBSTANCES, PRESENT IN A CONDUCTIVE LIQUID, DEVICE AND AFFINITY SENSOR USED FOR IMPLEMENTING SAID METHOD

(75) Inventors: Jean-René Martin, Lozanne (FR); Eliane Souteyrand, Ecully (FR)

(73) Assignees: Ecole Centrale de Lyon, Escully Cedex (FR); Centre National de la Recherche Scientifique (C.N.R.S), Paris Cedex (FR)

( * ) Notice: Subject to any disclaimer, the term of this patent is extended or adjusted under 35 U.S.C. 154(b) by 0 days.

(21) Appl. No.: 09/424,877
(22) PCT Filed: Jun. 11, 1999
(86) PCT No.: PCT/FR98/01213
  § 371 (c)(1),
  (2), (4) Date: Mar. 31, 2000
(87) PCT Pub. No.: WO98/57157
  PCT Pub. Date: Dec. 17, 1998

(30) Foreign Application Priority Data

Jun. 11, 1997 (FR) .............................. 97 07530

(51) Int. Cl.[7] ........................ G01N 27/26; G01N 27/00; C12Q 1/68; C12Q 1/04; C12Q 1/16
(52) U.S. Cl. ........................... 435/6; 204/403; 204/412; 324/71.5; 435/34; 435/35
(58) Field of Search ........................... 435/4, 6, 34, 39; 204/1, 403, 412; 324/71.5

(56) References Cited

U.S. PATENT DOCUMENTS 4,591,550 A * 5/1986 Hafeman et al. ............... 435/4
5,500,188 A * 3/1996 Hafeman et al. ......... 422/82.02

* cited by examiner

*Primary Examiner*—John S. Brusca
*Assistant Examiner*—Young Kim
(74) *Attorney, Agent, or Firm*—Dennison, Schultz & Dougherty (57) ABSTRACT

An apparatus and method for identifying and/or quantifying a charged biological substance in a conductive liquid medium.

26 Claims, 7 Drawing Sheets

METHOD FOR IDENTIFYING AND/OR ANALYZING BIOLOGICAL SUBSTANCES, PRESENT IN A CONDUCTIVE LIQUID, DEVICE AND AFFINITY SENSOR USED FOR IMPLEMENTING SAID METHOD

This is a 371 of PCT/FR98/01213 filed on Jun. 11, 1999.

TECHNICAL FIELD

The field of the invention is that of the detection of products, preferably "affinity" biological products, such as nucleic acids, or else biopolymers of a protein nature.

More specially, present invention relates, on the one hand, to a method for the qualitative and/or quantitative analysis of biological substances CBS, preferably polynucleotides PN present in a conductive liquid (solution or gel) medium CL, by means of optoelectrochemical measurements and, on the other hand, to the devices and the affinity sensors intended for implementing this method.

The biological substances more particularly, but not exclusively, for which the invention is targeted are polynucleotides PN. This general term encompasses, according to the invention, molecules composed of at least two nucleotides (oligonucleotides and polynucleotides stricto sensu), including especially the nucleic acids RNA or DNA and any genetic structure comprising them. The invention also relates to the compounds that can be involved in immunological coupling [antigen Ag/antibody Ab] reactions or even Enzyme/Substrate E/S recognition reactions.

PRIOR ART

In order to detect, identify or quantitatively determine these molecules, their bioaffinity properties. have been exploited, namely their particular ability to specifically pair with their complementary species, according to Ag/Ab immunological coupling or E/S recognition PN/cPN genetic hybridization mechanisms. Thus, in the immunological field, methods are known which are based on antigen/antibody coupling and which involve a step of revealing the pairs formed using radioactive, enzyme, fluorescent, colored or similar labels. Such methods are lengthy and complex to implement. In addition, the reactants used are not commonly available and are expensive. Finally, these methods do not allow continuous measurements and even less in vivo measurements. These techniques have been transposed with their shortcomings to the field of the detection of nucleic sequences, labeled in order to be able to be identified and/or quantitatively determined.

In another context, it has been proposed to detect physical signals of any kind that are capable of being induced by nucleotide-hybridization or immunological coupling biochemical reactions. To do this, it is appropriate, first of all, to isolate one type of particular and characteristic signal and then to use a transducer capable of converting said signals into a measurable physical quantity. These signals, may, for example, be produced by a chemical species, a variation in thickness, in optical index or in mass, or even a variation in electrical properties. The transducers may therefore be electrochemical, piezoelectric, optical or electrical sensors. The entire difficulty resides in how to bring out the specific signals from the pairing and how to develop a corresponding transducer which is reliable, sensitive and reproducible.

The invention described in French Patent Application No. 94/08688 falls perfectly within this prior art based on the detection of electrical signals induced by PN/cPN hybridizations or by antigen-antibody reactions, in an electrically conductive liquid medium.

That patent application describes a method for qualitatively and/or quantitatively analyzing biological substances, particularly polynucleotides, antigens, antibodies, enzymes and substrates, in which a multilayer structure comprising a semiconductor wafer is used, said wafer being covered with an insulator whose surface is functionalized by one of the species of the pairs of specifically pairable biological substances mentioned above. According to that method, the semiconductor containing polynucleotides PN to be quantitatively determined or to be identified are biased and the variations in the electrical signals induced by a charge effect phenomenon, directly and essentially related to the pairings of the intended biological substances with their complementary ligands immobilized on the insulator, possibly by means of a sensitive membrane, are collected.

This electrical transduction measurement technique does not require a reaction intermediate, a specific label, or an enzyme reaction. It gives satisfactory results but it nevertheless remains to be improved with regard to simplicity of implementation and capability of taking a series of rapid measurements on various substrates, without using as many sensors as there are different kinds of substrates to be analyzed. According to that technique, the charge-effect phenomenon may be apprehended by measuring the electrochemical impedance of a semiconductor/-insulator/sensitive membrane/conductive liquid structure. According to one embodiment, the field effect due to the variation in the surface charge induced by the pairing may be characterized by means of a biased field-effect transistor on which the variations in the gate/source potential induced by the field effect are measured.

Moreover, technical proposals have been made for the identification and/or quantitative determination of biological molecules, which combine

- on the one hand, means for revealing the substances to be quantitatively determined, using radioactive, enzyme, fluorescent or colored labels, redox-potential or pH modifiers, or similar means, and
- on the other hand, electrochemical or optoelectrochemical means of transduction.

Unfortunately, such a combination is not of the type to eliminate the drawbacks associated with the revelation-based techniques, nor to improve the electrochemical analysis techniques.

Thus, U.S. Pat. Nos. 4,591,550 and 5,500,188 disclose a method and a device for the determination and quantitative analysis of one or more substances which are contained in a gaseous or solid liquid medium and are capable of modifying the photoresponse characteristics of a photosensitive element, comprising means for recognizing said substances. These means involve a mechanism of revelation by one or more tracer substances capable of modifying the physicochemical characteristics of the analysis medium (pH or redox potential) and/or capable of being distinguished by a radioactive, colored or fluorescent label. It is therefore a hybrid technique which combines optoelectrochemical means of transduction with physicochemical means of revelation.

The device employed in that known method comprises one or more sensors each consisting of a semiconductor wafer (silicon covered with an $SiO_2$ or silicon nitride insulator layer), the surface of the latter possibly being functionalized by means for recognizing the substances to be identified and/or quantitatively determined. That device is also provided with means for biasing the semiconductor/insulator structure (e.g. a circuit for applying a biasing voltage, said circuit comprising, on the one hand, a counterelectrode and a reference electrode and being connected, on the other hand, to the semiconductor/insulator structure) The device furthermore includes means for irradiating the photosensitive element or elements as well as means for measuring the resulting electrical signals, for detecting and/ or for identifying the substances in question.

It should be noted that each photosensitive element comprising the semiconductor/insulator structure is necessarily associated with illumination means, biasing means and measurement means. It follows that the device is extremely complex in its alternative forms aimed at the multiple detection of different substances, both with regard to the structure as it is and to the taking and processing of the measurements and of the resulting signals.

According to this prior art, the insulator layer of the photosensitive elements is functionalized if the substances to be analyzed are PN/cPN, E/S or Ag/Ab affinity systems. In this case, the recognition ligands functionalizing the insulator layer are systematically labeled. This is illustrated especially in the case of DNA or RNA analysis, in which the complementary recognition ligands are labeled with biotin (cf. column 14, lines 49 to 63 of U.S. Pat. No. 5,500,188). In such configurations, all the drawbacks associated with these revelation techniques using a label must therefore be borne. Moreover, it should be pointed out that those techniques involving the absorption or emission of light radiation run the risk of further disturbing the intended activation irradiation according to this method.

If the systems are not affinity systems involving specific functionalization of the insulator of the sensors, the tracing means are, for example, variations in pH or in redox potential. These means should be considered as being not the most reliable since there are a good number of factors in the analysis medium, which is for example a conductive liquid, which can interfere with these parameters without this being connected with the identification and quantitative determination of the intended substances.

In addition, although the fact that the measured signal output by their sensors may be the photopotential, the photoconductance, the photocapacitance or the photoinductance, or combinations of these (column 3, lines 36 and 37 of U.S. Pat. No. 5,500,188) is not excluded, it is mentioned, in lines 41 to 43, column 3 of this same patent, that the measured signal is the resultant of a change in a DC current, of an AC current or of the effect of a DC current on an AC current. This preference for taking into account the photocurrent as the resulting signal is also clearly, and exclusively apparent from the examples of these U.S. patents which take into account either the current needed to maintain a constant potential between the sensitive element and the reference (column 19, lines 4 to 7), or the variations in this current, which correspond to the changes in the chemical environment in the region of the insulator of the sensitive element (column 19, lines 43 to 45), or the potential required for maintaining a constant current (column 19, lines 62 to 65) or the variation in the current supplied to the irradiation means necessary for maintaining a constant potential between the measurement structure and the reference (column 20, lines 42 to 49). This is also apparent from the passages in column 26, lines 7 to 9 and lines 30 to 34.

It is therefore apparent that the main signal taken into consideration in the method and the device according to patents U.S. Pat. No. 4,591,550 and 5,500,188 is the photocurrent measured either directly or indirectly. However, the relationship between the illumination and this photocurrent is poorly defined and involves several physical phenomena. This therefore results in uncertainty in the interpretation of the measurements.

It therefore has to be stated that this hybrid technical proposal mentioned above is in no way satisfactory in terms of the qualitative and/or quantitative analysis of substances, particularly biological substances, and even more particularly polynucleotide substances. Moreover, the Applicants wish to point out as proof of this that, there is at the present time on the market no industrial and commercial application of the invention described in these patents U.S. Pat. Nos. 4,591,550 and 5,500,188.

BRIEF DESCRIPTION OF THE INVENTION

Thus, in order to present the problematic at the heart of the present invention, the inventors are especially tasked, as essential objective, to provide a method for the identification and quantitative determination of biological substances, preferably polynucleotides, this method having to incorporate especially the following specifications:

specificity;

high sensitivity;

ease of implementation;

"applicability" to a wide variety of biological substances, and especially polynucleotide substances;

low manufacturing costs;

possible miniaturization so as to allow in situ and/or in vivo analytical measurements, continuously or intermittently;

high reliability, good reproducibility;

possibility of multiple detection, that is to say the identification and/or quantitative determination of different substances (heteroclite polynucleotides) contained in one and the same analysis medium;

application to the diagnosis of viral or genetic disorders, since it involves multiple detection which is simple to implement and interpret with respect to polynucleotides.

To meet these objectives, among others, the inventors have to their credit demonstrated, very surprisingly and unexpectedly, that the specific pairings between molecules, preferably biological molecules, and even more preferably between complementary polynucleotide strands, modify the surface electric charge in a multilayer-semiconductor Sc/surface-functionalized insulator Is-structure. This modification occurs more specifically at the interface with a conductive liquid medium CL, said charge effect constituting the base signal for identification and quantitative determination perceived, directly or indirectly, by optoelectrochemical transduction means.

The way in which this novel and advantageous concept is put into practice is expressed through the present invention, the subject of which is therefore a method for the identification and/or quantitative determination of Biological— preferably electrically Charged Biological—Substances (CBS) present in a Conductive Liquid medium CL, using at least one affinity sensor comprising at least one structure having at least one semiconductor material Sc coated on at least one of its faces with at least one layer of insulator Is, this layer having on its surface at least one probe Pr, in contact with the conductive medium CL and comprising one or more Recognition Biological Substances (RBS) for the specific recognition, by affinity interaction, of the CBSs in the abovementioned medium CL, which essentially consists in:

-a- selecting, as probe(s) Pr, unlabeled RBSs;

-b- taking measures to ensure that the Fermi level of the Sc corresponds approximately to, or passes by, the intrinsic level at the surface of the Sc;

-c- exposing the Sc to a periodic illumination comprising photons whose energy is greater than or equal to the band gap energy of the Sc;

-d- measuring, directly or indirectly, the variations $\Delta V_{fb}$ in the flat band potential $V_{fb}$ of the Sc, which are induced by a charge-effect phenomenon directly and essentially associated with the specific pairings of the CBSs in the conductive medium CL with their complementary ligands RBS of the probe or probes Pr, to the exclusion:

(i) of the variations resulting from possible charge and/or charge-transfer effects caused by enzyme-catalyzed chemical reactions in which some of the substances to be detected are consumed, (ii) and of the variations in the photoresponse which are associated with the appearance in the medium CL of at least one tracer product capable of being revealed through pH variations or redox potential variations and/or through labels, preferably of the type of those absorbing or emitting radiation (for example, fluorescent, radioactive or colored labels);

-e- and interpreting the received signals in terms of identification and/or quantitative determination of the CBSs in the CL.

Such a mode of measurement, by optoelectrochemical transduction, meets the desired specifications of simplicity, sensitivity, specificity, reliability and reproducibility.

Moreover, the technique according to the invention also has the advantage of being reversible. This is because it is readily possible to unpair the complementary species that have specifically reacted at the sensitive membrane of the semiconductor structure. The sensitive membrane may thus be regenerated after each use and this can be repeated many times.

Such advantageous results were a priori difficult to be able to predict.

In particular, this technique has proved to be remarkably effective in the context of the recognition of polynucleotide sequences by hybridization of the nucleic acid monostrands (ligands), which form these sequences, with complementary polynucleotide monostrands, immobilized on the layer of insulator of the Sc/Is structure. Thus, according to a preferred mode of implementing the method according to the invention, the CBSs are polynucleotides PN and the RBSs are polynucleotides cPN.

The present invention makes it possible to envisage, in particular, the recognition of nucleotide sequences, for example for the purpose of detecting genetic disorders, for detecting and characterizing viruses, bacteria and parasites, or for establishing genetic maps and for studying the expression and/or mutation of genes.

Apart from nucleotide hybridization, it is conceivable to exploit other specific pairings such as, for example, the biochemical mechanisms of immunological coupling or even of enzyme/substrate complexing, provided that the pairing results in a variation in electric charge at the surface of the Is.

DETAILED DESCRIPTION OF THE INVENTION

The analytical principle governing the method according to the invention is exclusively optoelectrical or optoelectrochemical. This means that there has to be affinity-type biochemical recognition, that is to say recognition which involves neither chemical nor enzymatic reactions and which takes place without the production or consumption of intermediate chemical species. Furthermore, the revelation of this affinity-type biochemical recognition does not occur through indirect detection using physicochemical means of revelation: colored, fluorescent, radioactive, redox-potential or pH tracers. According to the invention, the biochemical recognition takes place essentially, or even exclusively, by an optoelectronic transduction which involves biasing the Sc/Is structure with respect to the CL, as well as periodically illuminating said structure.

In the context of the invention, the expression "electrically charged" means that in the affinity interaction of the cPN with the PN, the surface electric charge is modified.

The first step -a- of the method according to the invention consists in employing exclusively probes Pr, particularly cPNs, which are not labeled, that is to say they do not carry physicochemical means of revelation (fluorescence, colorimetry, radioactivity, redox potential or pH).

In the case of a structure surface-functionalized by probes consisting of polynucleotide monostrands cPN, for example DNA, the hybridization of the latter with the strands to be identified or quantitatively determined in the medium CL involves an increase in the charges on the surface of the structure. This modifies the distribution of the charge carriers in the space-charge region of the semiconductor so as to satisfy the new thermodynamic equilibrium of the structure. This new distribution is manifested by a modification of the band curvature of the semiconductor in its interfacial region in contact with the dielectric. The flat-band potential $V_{fb}$ is the potential that has to be applied to the semiconductor with respect to the medium CL (the electrolyte) in contact with the dielectric Is in order for the bands of the Sc to have zero curvature. According to the invention, this physical quantity $V_{fb}$ or its variation $\Delta V_{fb}$ is measured so as to characterize the equilibrium state of the structure. Thus, a modification of the surface charge corresponds to a variation of $V_{fb}$, which is itself a signature of PN/cPN hybridization.

In order for there to be a variation in the curvature of the bands of the Sc and therefore in $V_{fb}$, it is necessary, in accordance with step b of the method according to the invention, to create an initial band curvature of the Sc by adjusting the Fermi levels of the Sc and of the medium CL, preferably by imposing a DC bias voltage $V_b$ on the Sc/Is-cPN structure with respect to the medium CL.

In accordance with a first mode of implementing the method according to the invention, the Fermi level of the semiconductor Sc is adjusted, to approximately its intrinsic level at the surface, by imposing a bias voltage $V_b$ on the Sc with respect to the CL by sweeping between a negative limiting voltage and a positive limiting voltage, these being chosen in such a way that the Fermi level of the Sc passes by its intrinsic level at the surface, $V_b$ thus advantageously varying within a voltage range corresponding to the depletion and weak-inversion regime of the Sc.

This DC biasing is associated, on the one hand, with the periodic illumination according to step c and, on the other hand, with a measurement of the $V_{fb}$ variations in step d. This measurement is carried out as follows:

detection of the photopotential ($V_{ph}$) at the terminals of the Sc (between Sc and CL) and/or of the photocurrent ($I_{ph}$);

calculation of the in-phase component $Z_{op}$ and/or the quadrature component $Z_{oq}$ of the optoelectrochemical impedance for each value of $V_b$;

construction of the $Z_{op}$ and/or $Z_{oq}$ and/or $V_{ph}$ and/or $I_{ph}$ curve/as a function of $V_b$;

and monitoring of the shift in this (or these) curve(s) parallel to the x-axis (potential $V_b$ axis), said shift corresponding to the desired variations in $V_{fb}$.

The optoelectrochemical impedance components $Z_{op}$ and $Z_{oq}$ are used to obtain the energy properties of the Sc/Is-Pr structure and of the interfacial region between said structure and the CL, and especially to obtain the various charge effects that may occur at the interfaces. These optoelectrochemical impedance components $Z_{op}$ and $Z_{oq}$ are linked to the photopotential $V_{ph}$ and the photocurrent $I_{hv}$ which are generated following the periodic luminous excitation of the Sc, the latter being, moreover, DC biased. This is because the modulated illumination (step c) of the Sc by photons having an energy greater than or equal to the width of its band gap generates electron-hole pairs or charge carriers. The latter are separated due to the effect of the electric field existing in the space-charge region of the semiconductor Sc (in the region in contact with the dielectric Is). This phenomenon causes the appearance of a periodic $I_{hv}$ in the semiconductor Sc, resulting, across the terminals of the Sc/Is-Pr structure, in a periodic photopotential $V_{ph}$ or a periodic photocurrent $I_{ph}$.

It is therefore possible to use, indiscriminately, $V_{ph}$ and/or $I_{ph}$ and/or the impedance components $Z_{op}$ and/or $Z_{oq}$ as transduction parameters of the charge-effect energy phenomena directly associated with the pairings of interest.

If the power of the illumination in step c is low, the optoelectrochemical impedance components $Z_{op}$ and $Z_{oq}$ are transfer functions linking $V_{ph}$ to $I_{hv}$ induced by the modulated illumination. More specifically, the optoelectrochemical impedance components $Z_{op}$ and $Z_{oq}$ near the space-charge region of the Sc are directly proportional to the effective values of the in-phase and quadrature components of the measured $V_{ph}$. The coefficient of proportionality depends on the intensity or power of the illumination.

The photopotential is therefore the image of the optoelectrochemical impedance of the structure.

In this version, it is preferred for the illumination to be not only weak but also approximately sinusoidal.

If the illumination employed at step c is strong, the $V_{fb}$ variations are obtained, in the context of step d, by preferably:

detecting $V_{ph}$ and/or $I_{ph}$ constructing the $V_{ph}=f(V_b)$ curve and/or the $I_{ph}=f(V_b)$ curve and monitoring the shift in this (or these) curve(s) parallel to the x-axis (potential $V_b$ axis), said shift corresponding to the desired $\Delta V_{fb}$ values. This is because, with strong illumination, if the surface charge varies because of the pairing of the PN in the CL with the cPNs in the probes Pr of the structure Sc/Is, it follows that there is a variation in $V_{fb}$ manifested by the curve of the effective value of the photopotential $V_{ph}$ and/or of the photocurrent $I_{ph}$ being shifted parallel to the axis on which the bias potentials of the structure are plotted.

According to the invention, the notions of weak and strong illumination are defined as follows:

weak illumination is illumination which results in a second-order perturbation of the structure with respect to the thermodynamic equilibrium in the dark. It is preferably less than or equal to 10 $\mu W/cm^2$ and preferably less than or equal to 1 $\mu W/cm^2$;

strong illumination is illumination which greatly perturbs the thermodynamic equilibrium of the structure in the dark. It is preferably greater than 10 $\mu W/cm^2$.

In the weak- and strong-illumination versions mentioned above, in the case of the description of the first mode of implementing the method according to the invention, the calculations of $Z_{op}$ and/or $Z_{oq}$, the controlling and acquisition of the measurements, and the plotting of the $Z_{op}$ and/or $Z_{oq}$ and/or $V_{ph}$ and/or $I_{ph}=f(V_b)$ curves are carried out by means of a microcomputer, using procedures known per se (especially calculation of the impedances according to Ohm's law).

In a second mode of implementing the method according to the invention, the following methodology is adopted:

in step b, the Fermi level of the Sc is set approximately to the intrinsic level at the surface of the Sc, by imposing a bias voltage $V_{bi}$ corresponding approximately to the abscissa of the point of inflection of the $V_{ph}=f(V_b)$ or $Z_{oq}=f(V_b)$ or $I_{ph}=f(V_b)$ curve, $V_{ph}$, $Z_{oq}$ and $I_{ph}$ being as defined above (page 9, lines 4 to 7), in such a way that the ordinate of this point of inflection corresponds approximately to $V_{ph,\frac{1}{2}max}$, $Z_{oq,\frac{1}{2}max}$ or $I_{ph,\frac{1}{2}max}$;

and in step d, the variations $\Delta V_{fb}$ in $V_{fb}$ are obtained:

(i) by measuring the change in $V_{ph}$ and/or $I_{ph}$ and/or $Z_{oq}$, if the variations $\Delta V_{fb}$ are small and assuming that $V_{fb}$ varies linearly with $V_{ph}$, then $\Delta V_{fb}=K\Delta V_{ph}$, where K represents the slope of the $V_{ph}=f(V_b)$ curve at the point of inflection;

(ii) and/or by taking into account the variations in the bias voltage $\Delta V_b$ made necessary in order to regulate, and keep constant, the $V_{ph,\frac{1}{2}max}$, the $Z_{oq,\frac{1}{2}max}$ or the $I_{ph,\frac{1}{2}max}$, this $\Delta V_b$ adjustment being the reflection of $\Delta V_{fb}$.

It is therefore a question, according to this mode of impementation, of biasing the Sc/Is structure in such a way that the Fermi level is in the vicinity of the intrinsic position of the semiconductor. The imposed potential $V_{bi}$ is close to the potential corresponding to the point of inflection of the sigmoidal-shaped curve of the photopotential $V_{ph}$, of the photocurrent $I_{ph}$ or the quadrature optoelectrochemical impedance component $Z_{oq}$ as a function of the bias potential $V_b$.

In the context of the invention, the expression "in the vicinity" of the Fermi level with respect to the intrinsic level at the surface of the Sc should be understood to mean the position close to the middle of the band gap of the semiconductor at its surface in contact with the insulator Is, within a range such that the semiconductor at the surface is in a depletion or weak-inversion situation, so that the photopotential $V_{ph}$ and/or the photocurrent $I_{ph}$ and/or the quadrature optoelectrochemical impedance component $Z_{oq}$ varies significantly with the bias potential $V_b$.

Thus, "$V_{bi}$ corresponding approximately to the potential at the point of inflection" should be understood, according to the invention, to be within a range of uncertainty of ±0.5 volts.

The ordinate of the point of inflection of these $V_{ph}$, $I_{ph}$ or $Z_{oq}=f(V_b)$ curves is advantageously chosen as a reference parameter to be kept constant within the context of this regulating by adjusting the $V_b$. The reference point is in practice given by the maximum value reached by $V_{ph}$, $I_{ph}$ or $Z_{oq}$ in each of the characteristic sigmoidal curves.

In other words, $V_{ph,max}$, $I_{ph,max}$ and $Z_{oq,max}$ correspond to the maximum value of the photopotential, the photocurrent and the quadrature optoelectrochemical impedance component, respectively, when the semiconductor is in a strong-inversion situation.

Insofar as the determination of the set value $V_{bi}$ involves taking into account the abscissa and the ordinate of the point of inflection of at least one of the $V_{ph}$ or $Z_{oq}$ or $I_{ph}=f(V_b)$ curves, it is envisaged in this second mode of impementation to construct at least one of said curves, preferably as described above in the case of the first mode of impementation.

Version (i) of step d according to this second mode of impementation consists in monitoring $\Delta V_{fb}$ by measuring the variation in $V_{ph}$, $I_{ph}$ or $Z_{oq}$ after calibration. This amounts to constructing the $V_{ph}$ and/or $I_{ph}$ and/or $Z_{oq}$=f(t) curve and to assuming that any $\Delta V_{ph}$, $\Delta I_{ph}$ or $\Delta Z_{oq}$ variation corresponds to a $\Delta V_{fb}$ variation. Version (i) can be used in the case of a moderate variation in $V_{fb}$, making it possible to establish a simple relationship (for example a linear relationship) between $\Delta V_{ph}$ and $\Delta V_{fb}$.

In practice, it is preferred to use version (ii) of step d according to the second mode of implementing the method according to the invention. In this version, $V_{ph,\frac{1}{2}max}$ is kept constant by adjusting the bias potential $V_b$ of the structure, preferably by means of electronic regulation.

The regulation $\Delta V_b$ corresponds to the $\Delta V_{fb}$ that it is desired to measure.

According to an advantageous arrangement of the invention, the electronic regulation that may be used within the context of version (ii) of taking $\Delta V_b$ into account is carried out in the following manner:

$V_{ph}$ is detected;

optionally, the signal $V_{ph}$ is amplified;

optionally, this signal is rectified so as to give a DC signal $V'_{ph}$;

this DC signal $V'_{ph}$ is compared with a reference signal U corresponding approximately to the value of $V'_{ph,\frac{1}{2}max}$ (the ordinate of the point of inflection of the curve $V'_{ph}$=f($V_b$), i.e. $V'_{ph,\frac{1}{2}max}$);

the difference between $V'_{ph}$ and U, namely $\Delta(V'_{ph}-U)$, is obtained;

optionally, $\Delta(V'_{ph}-U)$ is amplified;

the optionally amplified $\Delta(V'_{ph}-U)$ is applied between Sc and CL as a complement of $V_b$;

$\Delta(V'_{ph}-U)$ is recorded.

The advantage of such a regulating procedure stems from the fact that the electrically imposed potential is directly and linearly the image of the $V_{fb}$ variations caused by the interactions on the surface of the dielectric Is. It is therefore independent of the properties of the structure and allows good sensitivity and excellent measurement reproducibility to be obtained.

According to the nomenclature adopted in the present description, $V_{ph}$ denotes both the primary photopotential $V_{ph}$ measured between Sc and CL and the $V'_{ph}$ corresponding to the rectified and optionally amplified $V_{ph}$.

With regard to the illumination step c, which is common to both the abovementioned modes of implementation, it should be pointed out that said illumination may be carried out opposite any region of the external faces of the Sc/Is-Pr structure, including, where appropriate, on its thickness, or even over the entire external surface of this structure.

In other words, the periodic illumination of the Sc/Is structure is therefore carried out opposite the external face or faces of the Sc, or opposite the external face or faces of the insulator Is or opposite all the external faces of the structure.

In the case of step c, the wavelength $\lambda$ of the illumination is preferably chosen so that it is greater than or equal to $$\lambda_0 = \frac{1240}{E\text{ (band gap energy)}} \text{ nm,}$$

and preferably between 100 and 3000 nm, E being the band gap energy of the Sc expressed in electron volts.

This threshold $\lambda_0$ depends on the nature of the semiconductor.

According to a third way of implementing the method according to the invention, the nonspecific responses maybe radically removed by employing a differential measurement in which at least one other reference structure Sc/Is is used in the affinity sensor, in which Is is not functionalized by Pr, and by monitoring the difference between the $V_{fb}$ variations measured by the 2 sensors, as well as the variation in this difference.

In this third mode of impementation, the measurement structure Sc/Is-Pr and the reference structure Sc/Is are brought into contact with the same medium CL. They are biased in the same way, preferably by means of the same counterelectrode, a reference electrode not being necessary. Finally, in accordance with step c, they are exposed to the same modulated-light illumination.

Moreover, the means for interpreting the detected signals used in step d are chosen so as to make it possible to monitor the difference between the flat band potentials $V_{fb0}$ and $V_{fb1}$ specific to the two structures, Sc/Is and Sc/Is-Pr, respectively.

This arrangement makes it possible to obtain a very precise and continuous measurement of the variation in $V_{fb1}$ of the functionalized structure Sc/Is-Pr, by overcoming the spurious effects which may occur and are associated with parameters other than the pairing, and in particular other than the PN/cPN hybridization.

A fourth way of implementing the method according to the invention is one in which, in a prior step $a_0$, various regions on the surface of a layer of insulator Is of the same structure Sc/Is are functionalized by several probes Pr which differ in the nature of the cPNs of which they are composed and then, using this structure, the CL containing one or various PN substrates is analyzed:

by illuminating, in succession, the regions of the surface of the Is, said regions each being functionalized by the same Pr (identical cPNs), the nature of the Prs varying from one region to another;

and by measuring and interpreting the $\Delta V_{fb}$ variations.

This fourth mode of impementation corresponds to the multiple detection of substrates, particularly PN substrates, of different kinds, within the genetics field. The multiple detection according to the invention makes it possible to use simple and rapid methods for detecting viral disorders and genetic disorders. It is also conceivable to make checks of histocompatibility, as well as the mapping of heterogeneous populations of polynucleotides, for example of genomes. This furthermore constitutes a tool for studying gene mutation, gene expression or genome sequencing.

The advantage of multiple detection according to this fourth mode of implementation lies in the methodological and structural simplicity of the corresponding method and the corresponding device.

The advantage of multiple detection according to this fourth mode of implementation lies in the methodological and structural simplicity of the corresponding method and the corresponding device.

In a manner common to the third and fourth modes of implementation mentioned above, namely differential measurement and, multiple detection respectively, it should be pointed out that the, step of measuring $\Delta V_{fb}$ directly or indirectly may be carried out according to the procedure described in the case of the first mode of implementation in one or other of these weak- or strong-illumination versions, and likewise according to the procedure specific to the second mode of implementation, whether it is version (i) or version (ii) that is adopted.

The Invention is a measurement method founded on the recognition of the variation in the flat band potential ($\Delta V_{fb}$)

of a structure Sc/Is-Pr having a sensitive region made of probes Pr based on recognition biological substances RBS (e.g. cPNs) capable of reacting specifically with electrically charged biological substances CBS (e.g. PNs) in a medium CL.

Advantageously, the substrates to be analyzed are PNs, preferably chosen from the following list: nucleotides, oligonucleotides, polynucleotides, nucleic acids (DNA or RNA) as well as similar materials and mixtures of said substrates.

According to the invention, the probes Pr employed in the method are means of specific recognition, particularly of unlabeled cPNs, that is to say those not carrying means of revealing the PN/cPN pairing (fluorescence, colorimetry or radioactivity).

Although preference is given to biological substances of the polynucleotide-sequence type (RNA, DNA, gene, plasmid or any other genetic material), this does not in any way exclude other biological substances of the antigen, hapten or antibody type or, more generally, any species of a couple formed by a biological macromolecule and its specific complement. As examples of specific-pairing couples or pairs, mention may be made of: antigen/antibody, hapten/antibody, cDNA/DNA, cRNA/RNA, poly (dT)/mRNA eukaryotic or lectin-glyco-conjugated, cell (or microorganism) marker/cell (or microorganism), HcG/tissue receptor and T3/TGB (thyroxin binding protein).

The method according to the invention firstly involves the immobilization of at least one type of these reactive biological species cPN in order to form the probe or probes Pr. The immobilization may be carried out directly on the insulating layer or using an intermediate material (for example spacing compounds) fastened to the insulator Is and capable of receiving, by physical bonding (e.g. adsorption/absorption) and/or chemical bonding (e.g. covalent bond), the specific biological ligands cPN.

According to the invention, it is completely conceivable to provide one of the heterospecific probes Pr formed from biological species CPN of different types, which are capable of reacting with their complementary species.

The conductive liquid medium CL may be any buffer solution compatible with the biological substances PN in question. This liquid medium CL advantageously has a conductivity equivalent to that of an aqueous NaCl solution having a concentration that can range from 0.005M to 3M and preferably about 0.1M.

The pH of the liquid medium may be between 0 and 12, preferably between 6 and 8, so as to favor the pairings by bioaffinity. The harshness of the liquid medium may also be adjusted in order to favor hybridization.

The nonspecific interactions, by exchange of ions or by hydrophobic interactions, may be eliminated completely or partly using a buffer of suitable ionic force (e.g. Tris-HCl/Tris-base).

Advantageously, the measurement temperature may be between 0 and 50° C. It is controlled more precisely so as to favor the biochemical reactions in question.

The subject of the invention is also a device for implementing the method as described above, said device being one which comprises:

at least one affinity sensor formed by at least one structure Sc/Is-Pr in which the probe or probes Pr comprise ligands RBS suitable for being specifically hybridized with the biological substances CBS to be analyzed, these being contained in the conductive liquid medium CL, by causing a charge-effect phenomenon giving rise to the $\Delta V_{fb}$ variations of the Sc;

means for biasing the Sc with respect to the CL;

means for illuminating the Sc of the sensor;

means for measuring the photopotential $V_{ph}$ or the photocurrent $I_{ph}$;

means for converting the detected signals into $V_{fb}$ variations;

and means for calculating and interpreting the $\Delta V_{fb}$ variations in terms of the identification and/or quantitative determination of the biological substances CBS.

Roughly speaking, this device therefore comprises:

firstly, one or more simple semiconductor multilayer structures that can be likened to measurement electrodes;

secondly, a source of modulated light for illuminating this or these structures; and thirdly, electronic peripheral means for electrical biasing, for measurement, for calculation and for interpretation.

The measurements of the photopotential $V_{ph}$ and/or the in-phase optoelectrochemical impedance component $Z_{op}$ and/or quadrature optoelectrochemical impedance component $Z_{oq}$ are carried out in an open-circuit configuration, that is to say the measurement circuit must have a very high load impedance.

The measurements of the photocurrent $I_{ph}$ are advantageously carried out in a closed-circuit configuration (short circuit).

These technical means involve conventional technologies fully controlled by those skilled in the art.

Furthermore, this device benefits from a low manufacturing cost. It may be easily produced on an industrial scale and offers high reliability and good measurement reproducibility.

In addition, the already miniaturized, or indeed "miniaturizable", character of the affinity sensors constituting the device opens up promising future prospects, especially for certain in vivo or in vitro applications.

Preferably, but nonlimitingly, the measurement electrode (that is to say the multilayer structure Sc/Is-Pr) of the affinity sensor of the device is formed by at least one wafer of Sc, preferably made of silicon, covered on one of its faces with at least one layer of insulator, Is, preferably silica, fastened to the surface of which is at least one sensitive probe Pr comprising at least one biospecific pairing ligand, preferably polynucleotides cPN for specific recognition by hybridization, this sensor also having at least one ohmic contact allowing connection of the structure Sc/Is-Pr, especially to the biasing means and/or the means for measuring $V_{ph}$.

The device furthermore comprises this structure Sc/Is-Pr, at least one auxiliary electrode, possibly provided on the layer Is of the structure Sc/Is-Pr.

Advantageously, the layer of blocking dielectric material Is is for example, a layer of oxide and/or of nitride or any other inorganic or organic material of small thickness, preventing or limiting the faradaic phenomena. This structure is associated with a conductive liquid medium CL containing the substances CBS to be detected or identified or quantitatively determined.

In practice, the silicon chosen as semiconductor is of the n or p type and is moderately doped, preferably to a level of $10^{15}$ to $10^{19}$ cm$^{-3}$, preferably $10^{16}$ cm$^{-3}$. The thickness of the silicon wafer is, for example, between 0.01 and 2 mm.

The insulating layer Is advantageously consists of silica or silicon nitride. Its function is to cancel out any faradaic process which might disturb the measurements, by means of spurious electrical signals. This layer Is also prevents the difficulties associated with possible corrosion of the semiconductor material by the conductive medium CL in contact with it. The thickness of this layer Is is between 1 and 500 nanometers, preferably between 1 and 50 and even more preferably about 10 nanometers.

The dielectric layer Is supports the probes cPN-Pr, which probes constitute what might be called a bioreceptive membrane in contact with the medium CL.

DESCRIPTION OF THE FIGURES

the appended

the appended

The present invention will be understood in the light of the following description, the embodiments of the device and the modes of implementing the method to which the invention applies, with reference to the appended drawings. These nonlimiting illustrations bring out many advantages and versions of the invention.

Figure 1:
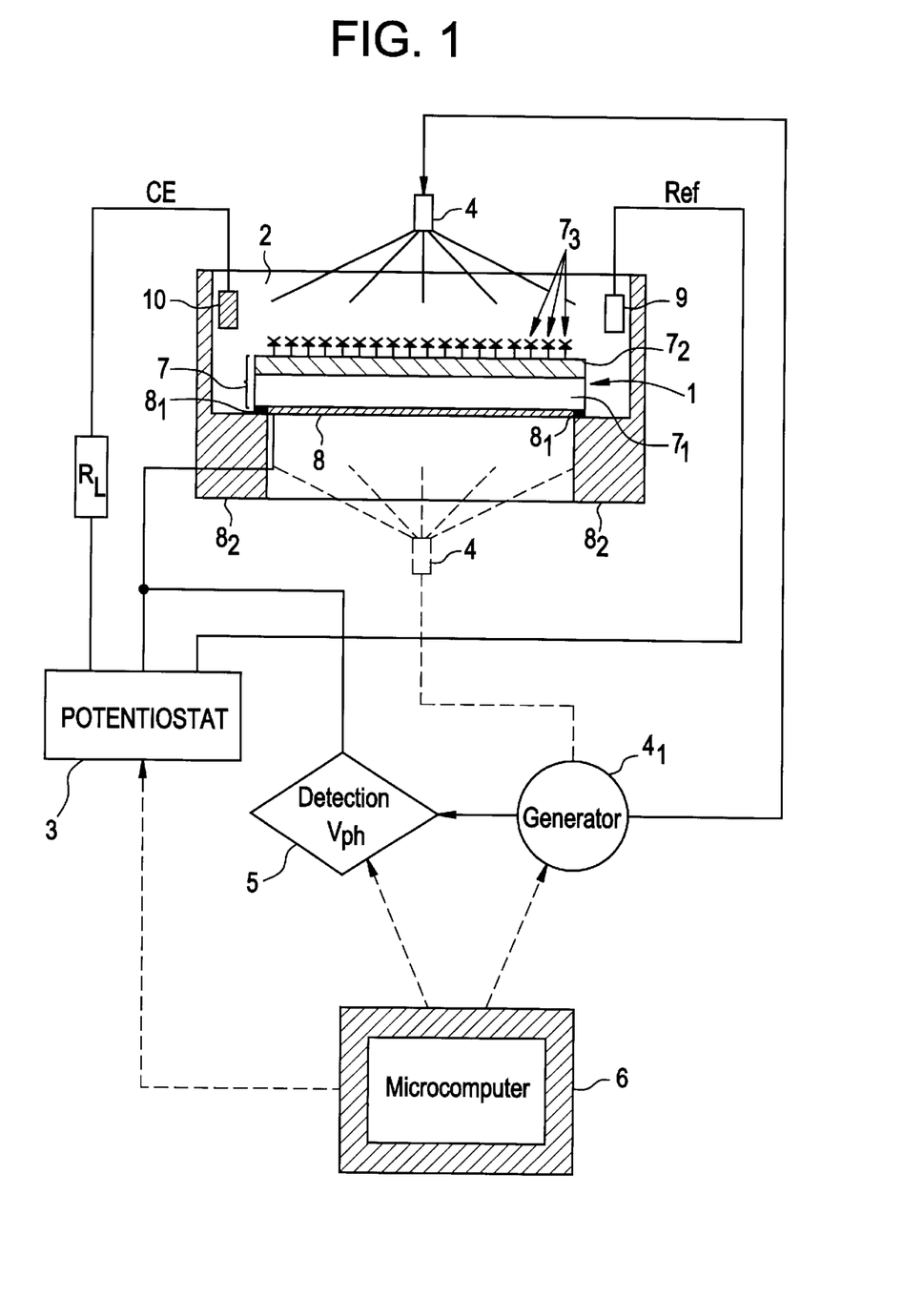
FIG. 1 is a schematic representation of the device for qualitatively and/or quantitatively analyzing biological substances, preferably polynucleotides PN present in a conductive liquid medium CL according to the invention.

FIG. 1 shows the device according to the invention, which comprises an affinity sensor 1 formed by a structure 7 Sc/Is-Pr in contact, via its face supporting the Prs, with a conductive liquid medium CL denoted by the reference 2. This device also includes biasing means 3, illumination means 4, means 5 for measuring $V_{ph}$ and a computing and control unit 6 comprising means for converting the received signals into $V_{fb}$ variations and means for calculating and interpreting the $\Delta V_{fb}$ variations in terms of the identification and/or quantitative determination of the electrically charged biological substances to be analyzed, also called CBSs. The affinity sensor 1 consists of a structure 7 Sc/Is-Pr, which is itself formed by a wafer Sc of silicon 7.1, a layer of insulator Is made of silica 7.2 and probes Pr which are denoted by the reference 7.3 and are fastened to the surface of the insulator Is 7.2 in order to functionalize the latter. According to one version, a functional layer may optionally be deposited on the surface, allowing the probes Pr to be more strongly attached. The affinity sensor 1 is provided, on its external face opposite that carrying the probes Pr 7.3, with an ohmic contact a connected to the biasing means 3. The ohmic contact 8 is isolated from the medium CL 2 by a peripheral seal 8₁. The latter engages with an insulating support 8₂ so as to produce a sealed contact, the sensor 1 in its entirety resting on said insulating support. Advantageously, these probes consist of Recognition Biological Substances (RBS) for the specific recognition of the CBSs. In the present example, the CBSs and the RBSs are polynucleotides PN and cPN.

A reference electrode 9 and a counterelectrode 10 are also immersed within the conductive liquid medium CL 2 with the affinity sensor 1. These two electrodes 9 and are connected to the biasing means 3.

In accordance with a preferred characteristic of the invention, a high load resistance is provided in the potentiostatic measurement circuit. Advantageously, a resistor having this high resistance $R_L$ is inserted into the connection linking the counterelectrode to the biasing means 3. In practice, the resistance $R_L$ is preferably greater than 100 kΩ, preferably 50 MΩ and even more preferably is about 100 MΩ.

Figure 2:
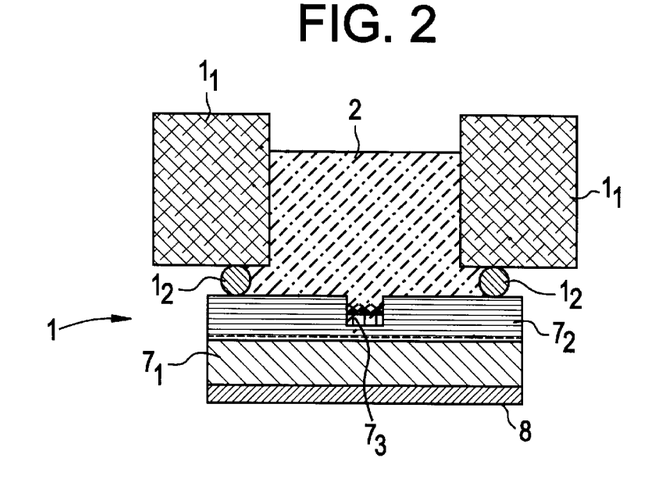
FIGS. 2 and 3 are cross-sectional views of embodiments of the affinity sensor shown in FIG. 1.
Figure 3:
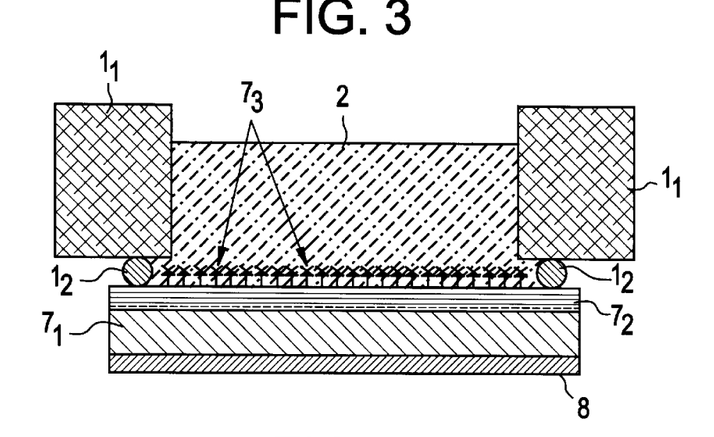

FIGS. 2 and 3 each show an illustrative embodiment of the affinity sensor 1 in which the structure 7 constitutes the bottom of a measurement cell comprising walls 1₁ and a seal 1₂ which seals between the bottom 7 and said walls 1₁.

The elements common to FIGS. 1 to 3 are denoted by the same reference numbers.

The version of FIG. 2 is distinguished from that of FIG. 3 in that the sensitive region comprising the probes Pr 7₃ is delimited in the first case but not in the second (the entire surface of the Is has probes Pr 7₃). The biasing means 3 of the device according to the invention preferably consist of a matched potentiostat having, for example, a long time constant (greater than 1 s). It allows the structure to be biased, while at the same time not disturbing the photopotential $V_{ph}$.

In the example shown in the block diagram of FIG. 1, which corresponds to a preferred form of the invention, the illumination means 4 comprise at least one light source, in this case one source, placed either facing the bioreceptive membrane 7.3 formed by the probes Pr fastened to the insulator Is 7.2, or facing the face of the Sc 7.1 on the opposite side from the face 7.3 which carries the ohmic contact 8 (the situation shown symbolically by dotted lines in the diagram of FIG. 1), or facing all or part of the outside of the structure 7.

This light source 4 consists, for example, of a laser such as a helium-neon laser having an emission wavelength of 632.8 nm.

Advantageously, the light beam passes through an acoustooptic modulator (not illustrated in FIG. 1), the controller of which is run by a low-frequency generator, denoted by the reference 4.1 in FIG. 1.

A filter (not illustrated) makes it possible to adjust the luminous power to values of less than, equal to or greater than the threshold which determines the weak-illumination and strong-illumination ranges. Preferably, the luminous power is of the order of or less than or equal to 1 $\mu W/cm^2$ under the weak-illumination conditions and greater than 10 $\mu W/cm^2$ in the case of strong illumination.

In practice, the means 5 for measuring $V_{ph}$ consist, for example, of an impedance matcher having an input impedance of between $10^8$ Ω and $10^{12}$ Ω, more preferably of the order of $10^{10}$ Ω.

The measurement means 5 also comprise a synchronous detection member run by the low-frequency generator 4.1 which, as was seen above, also determines the modulation of the illumination. This synchronous detection member gives the in-phase and quadrature components of $V_{ph}$.

The microcomputer 6 comprises the means for converting the received signals into $V_{fb}$ variations as well as the means for calculating and interpreting $\Delta V_{fb}$ in terms of the identification and/or quantitative determination of biological substances, in this case polynucleotides PN. The diagram of the electrical measurement circuit is illustrated in FIG. 4.

In the weak-illumination version, the optoelectrochemical impedance components $Z_{op}$ and $Z_{oq}$ are the transfer functions which link $V_{ph}$ to the intensity of the illumination.

Figure 4:
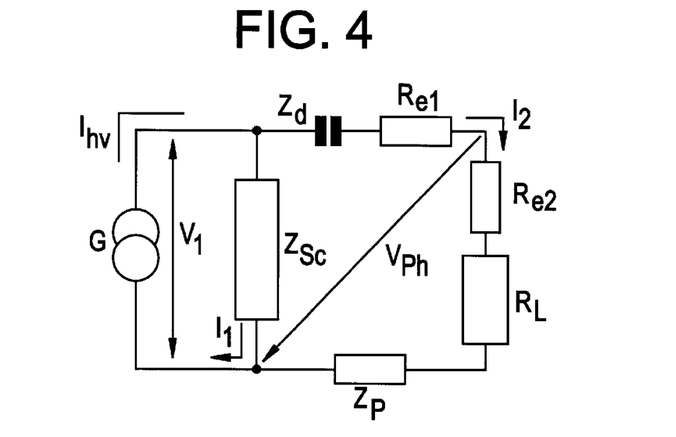
FIG. 4 shows the diagram of the electrical circuit for measuring the optoelectrochemical impedance components $Z_{op}$ and $Z_{oq}$ of the affinity sensor according to the invention, according to the first mode of implementing the method, in its weak-illumination version.

As shown in FIG. 4, the effect of the illumination may be represented by a current generator in parallel with the space-charge region, the impedance of which, denoted by $Z_{sc}$, includes the parameters associated with the surface. $Z_d$ is the impedance of the dielectric. It may be represented by a pure capacitance. $R_{e1}$ and $R_{e2}$ are the impedances of the electrolytic solution between the working electrode and the reference electrode, and between the reference electrode and the counter-electrode, respectively. $Z_p$ is the internal resistance of the potentiostat. $R_L$ is the load resistor introduced into the potentiostatic measurement circuit. Its role is to give the measurement circuit the properties of a circuit which is almost open with respect to the photopotential, while at the same time allowing the structure to be biased; its value must therefore be sufficiently high with respect to the other impedances involved in the measurement. $V_{ph}$ is the measured photopotential and $V_1$ is the photopotential which appears across the terminals of the semiconductor. According to the electrical circuit diagram, the total current $I_{hv}$ generated by the illumination has two components: $I_1$ which passes through the semiconductor and $I_2$ which flows in the measurement circuit. The following equations may therefore be written:

$$I_{hv}=I_1+I_2=(V_1/Z_{sc})+(V_1/(R_L+R_{e1}+R_{e2}+Z_d+Z_p)) \text{ if } R_L>>R_{e1}+R_{e2}+Z_d+Z_p \text{ then:}$$

$$V_{ph}=V_1 \text{ and } I_{hv}=(V_{ph}/Z_{sc})+(V_{ph}/R_L)$$

where $Z_{sc}=V_{ph}/I_{hv}$.

Thus, the in-phase and quadrature optoelectrochemical impedance components near the space-charge region of the semiconductor are directly proportional to the components of the measured photopotential: the coefficient of proportionality depends on the intensity of the illumination.

The measurement of the optoelectrochemical impedance components can therefore be used for detecting the pairing process, particularly a process of pairing by PN/cPN hybridization, said process being the quantitative and qualitative reflection of the CBS(PN)s to be analyzed.

Examples 1 and 2 below illustrate the weak-illumination version of the first mode of implementing the method according to the invention.

Regarding the strong-illumination version of this first mode, it consists in obtaining the variations in the flat band potential $V_{fb}$ of the Sc, as a result of the biological recognition phenomenon, by means of the effective value of $V_{ph}$ (or, according to an alternative version, of $I_{ph}$). In this case, the modulated, is not necessarily sinusoidal, but it may simply be periodic. Thus, in the device of FIG. 1, if the surface charge varies with the presence of the target species PN in the medium CL denoted by the reference 2, this results in a $\Delta V_{fb}$ which is manifested by a shift in the curve of the effective value of $V_{ph}$, parallel to the axis on which the potentials for biasing the structure are plotted.

Example 3 below illustrates this strong-illumination version of the first mode of implementing the method of the invention, using the matched device.

According to the second mode of implementing the method of the invention, the structure SC/Is-Pr is biased in such a way that the Fermi level of the Sc is in the vicinity of the intrinsic position of the surface of the Sc. The potential $V_b$ then imposed is close to the potential corresponding to the point of inflection of the sigmoidal-shaped curve of the effective value of $V_{ph}$, of $I_{ph}$ or of $Z_{oq}$.

Measuring the variation in the effective value of $V_{ph}$, of $I_{ph}$ or of $Z_{oq}$ after calibration allows the $\Delta V_{fb}$ to be obtained.

According to version (ii), the effective value of $V_{ph}$ is set to a value close to its $V_{ph,\frac{1}{2}max}$ ($=V_{phi}$) value by varying the initial DC bias, which will be a set value $V_{bi}$. The effective value of $V_{phi} I_{phi}$ or $Z_{oqi}$ is then kept constant by adjusting $V_b$ with respect to the set value $V_{bi}$ of the structure, by means of electronic regulation. This adjustment of the bias is the direct image of $\Delta V_{fb}$. The effective values of $V_{ph}$, $I_{ph}$ and $Z_{oq}$ are $V_{ph,\frac{1}{2}max}$, $I_{ph,\frac{1}{2}max}$ and $Z_{oq,\frac{1}{2}max}$, respectively. They each represent approximately the ordinate of the point of inflection of the corresponding curve.

Example 4 illustrates the second mode of implementation, without strong illumination, in version (ii).

For the implementation of this version (ii), one particular embodiment of the device according to the invention is used, this being one in which it comprises means for evaluating the variation in the $V_{ph}$ or $I_{ph}$ or $Z_{oq}$ signal with respect to a reference U imposed by a bias $V_b$, which is superadded to the illumination, as well as means for correcting and regulating the variation by acting on the biasing means.

Figure 5:
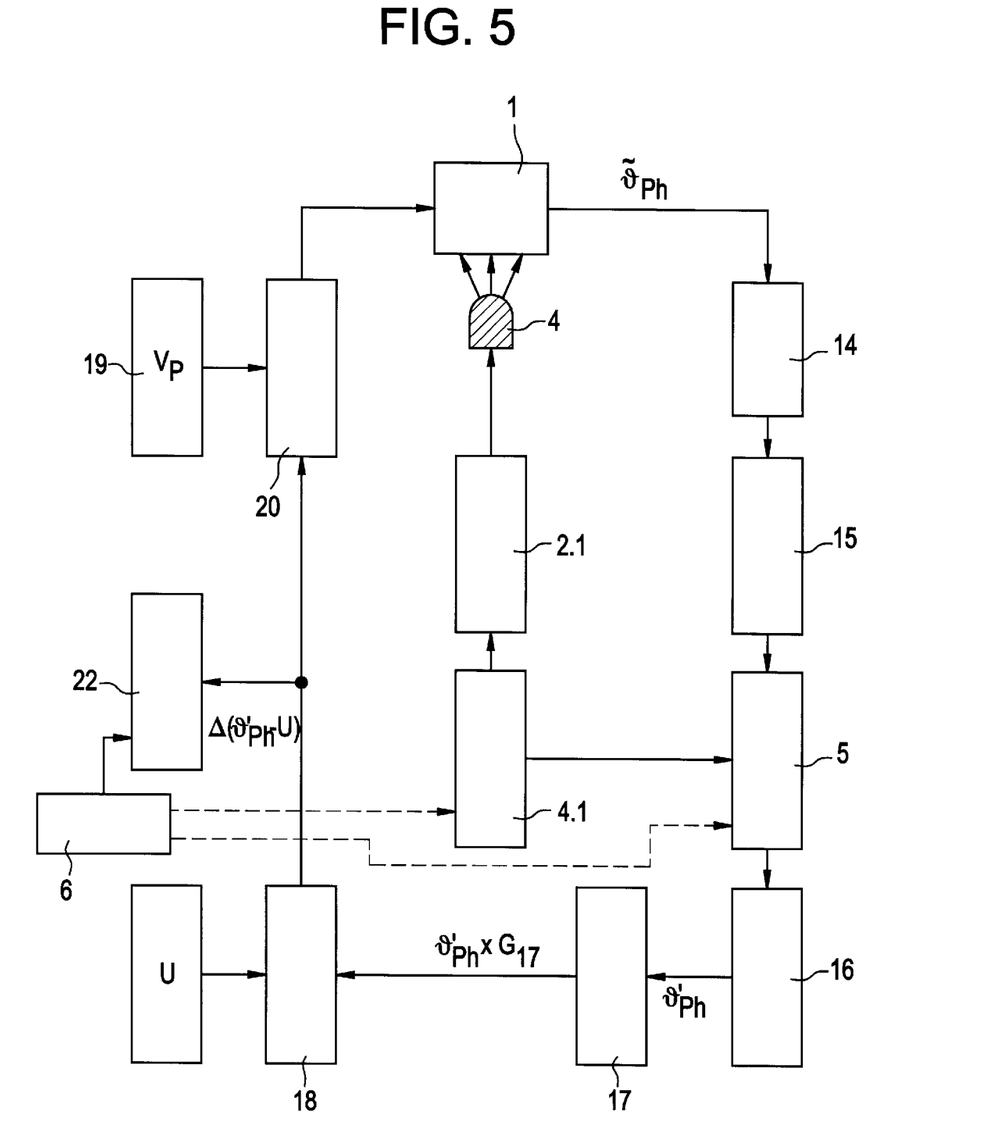
FIG. 5 shows the block diagram of one particular embodiment of the measurement device according to the invention, corresponding to version ii of the second mode of implementing the method according to the invention.

The appended FIG. 5 shows the block diagram of an example of this particular embodiment of the device according to the invention. In this example, $V_{ph}$ is chosen as the tracer signal.

As shown in this FIG. 5, in which the elements common to those in FIG. 1 are referenced by the same reference numbers, the photopotential $V_{ph}$ is detected at the terminals of the affinity sensor 1 (measurement cell) by means of an impedance matcher 14 having a high input impedance so as not to disturb the structure. The signal is then amplified by means of a low-frequency AC amplifier 15 and converted into a DC signal $V'_{ph}$ by means of a synchronous detection circuit 5 and of an RC circuit 16 which makes it possible to reduce the noise and to stabilize the regulation.

The DC signal $V'_{ph}$ is amplified by means of a DC amplifier 17 having a gain $G_{17}$. G1 is the gain of the combination of the amplifiers 15 and 17 and of the synchronous detection circuit 5. The amplified DC signal $V'_{ph}$ is then compared with a reference signal U using a differential amplifier 18. U is set to the value of $V_{bi}$ which makes the photopotential have a value half that of the photopotential corresponding to strong inversion ($V_{ph,\frac{1}{2}max}$). The residual difference in value $\Delta(V'_{ph}-U)$ between these two signals is amplified by the differential, amplifier 18 having a gain G2 and the output voltage $\Delta(V'_{ph}-U)$ is applied to the structure 1 at the same time as the DC bias $V_b$ imposed by a voltage generator 19 coupled to a summer 20. A low-frequency (LF) signal generator 4.1 makes it possible, after amplification using an amplifier 2.1, to control the diode 4, the beam of which excites the structure 1, and also to reference the synchronous detection circuit 5. The microcomputer 6, which is especially linked to a member 22 for the acquisition of the variable $\Delta(V'_{ph}-U)$, makes it possible to monitor and record the variation in the bias of the structure $\Delta V_b$ caused by the variation in the flat band potential ($\Delta V_{fb}$).

The advantage of such a set-up is that the electronically imposed potential is, directly and linearly, the image of the variations in the flat band potential $V_{fb}$ which are caused by the interactions at the surface of the dielectric. It is therefore independent of the properties of the structure and makes it possible to obtain good sensitivity and excellent reproducibility.

The cell (sensor) is similar to that described above with reference to FIG. 1.

Since the photopotential is measured by means of a measurement circuit having a high input impedance, it is possible to accept an ohmic contact of mediocre quality. In order to measure the photopotential of the semiconductor with respect to the solution, an electrode having a constant potential with respect to the solution is needed. However, because of the high impedance of the measurement circuit, it is possible to use a pseudo reference electrode consisting of a noble metal, such as platinum for example. The electrode may be independent or may be produced by deposition, in the form of a grid or of an external ring, on the surface of the dielectric so as to comply with the miniaturization of the sensor.

The structure may be illuminated by means of a laser diode or a light-emitting diode emitting in the visible or very near-infrared wavelength range, between 400 and 1000 nm, with a luminous power of the order of 0.1 to 100 $\mu W/cm^2$. It is technologically quite conceivable to envisage illuminating the structure via the rear face and even to integrate the light-generating part into the sensor. These technical options would make it possible to have a sensor of very small size, only the front face of which would be in contact with the solution and which would thus be, because of the nature of the materials of which it is composed, very insensitive to chemical etching.

It is quite possible to use $I_{ph}$ as the tracer signal. In this case, the impedance matcher 14 is replaced by a current-voltage converter.

The embodiments of the device according to the invention which are illustrated in FIGS. 1 and 5 described above are arbitrarily called GENOPTEL.

In another embodiment of the device according to the invention, corresponding to the third mode of implementing the method, said device is one in which the affinity sensor comprises at least one structure Sc/Is-Pr and at least one reference structure Sc/Is not functionalized by Pr, so as to be able to carry out a differential measurement.

Figure 6:
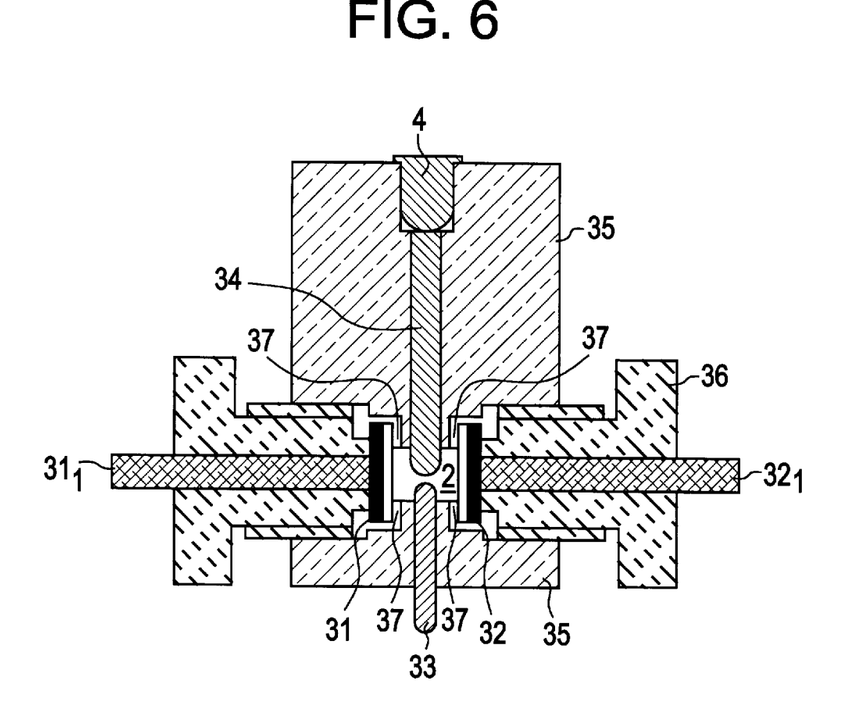
FIG. 6 is a schematic cross-sectional representation of an embodiment of the device according to the invention, namely the differential sensor corresponding to the third mode of implementing the method.

This embodiment, which will be called DIGENOPT is illustrated in FIG. 6. It corresponds to the case in which there is an affinity sensor 1, or measurement cell, advantageously comprising two almost identical structures Sc/Is 31 and 32, one being functionalized by Pr and the other not. These two structures (or electrodes) are brought into contact with the same medium CL 2 and are biased by means of the same counterelectrode 33. A reference electrode is not needed. The structures are illuminated in an identical fashion by modulated light delivered by a diode 4. The light travels to the medium CL 2 via an optical conductor 34 provided through the body 35 of the sensor 1.

The two structures Sc/Is 31 and 32 (electrodes) are each mounted on the end of an element 36 which can be screwed into the body 35 of the sensor 1.

The body 35 comprises a cavity, closed laterally by the electrodes 31 and 32, which contains the medium CL 2.

Seals 37 are provided in order to seal between the various walls. The top wall accommodates the illumination means 4 and 34. The counterelectrode 33 passes through the bottom. The matched electronic peripheral means make it possible to monitor the difference in their respective $V_{fb}$ ($=V_{fb1}-V_{fb0}$).

A nonlimiting illustration of the device of the invention will be concluded by describing a final, but not the least, embodiment which is that in which the device is one where the affinity sensor comprises at least one structure Sc/Is-Pr in which the probes Pr are of various types, the probes Pr of the same type being grouped together in the same region of the layer of Is, each region being circumscribed with respect to the others so as to be able to be separately illuminated, partially or completely, by the illumination means.

This embodiment, arbitrarily denoted by the expression GENMAP, has been made possible because of the fact that the principle of the measurement according to the invention is such that the photopotential and/or the photocurrent depends on the light flux but it is virtually independent of the area of the surface illuminated. It is therefore conceivable to produce, on the same structure Sc/Is, differently functionalized regions which respond in a specific manner to various target species (e.g. $PN_1$ to $PN_n$), the pairing or the hybridization being read by means of a light beam, by successively or simultaneously scanning using several light beams.

Such a structure Sc/Is can be likened to a biological multisensor allowing multiple detection.

The various regions of the surface of the Is may or may not be physically bounded.

Multiregion reading by the illumination means makes it possible to obtain the local flat band potential of each specifically functionalized region:

either by measuring the optoelectrochemical impedance according to the first mode of implementation, in the weak-illumination version or the strong-illumination version;

or by measuring the effective value of $V_{ph}$ in version (i) of the second mode of implementation;

or by taking account of the variations in $V_b$ allowing $V_{ph}$ to be regulated and maintained at a value close to its mean value (version (ii) of the second mode of implementation).

In other words, the, acquisition of $V_{fb}$ may be achieved according to any one of the modes of implementing the method according to the invention.

Figure 7:
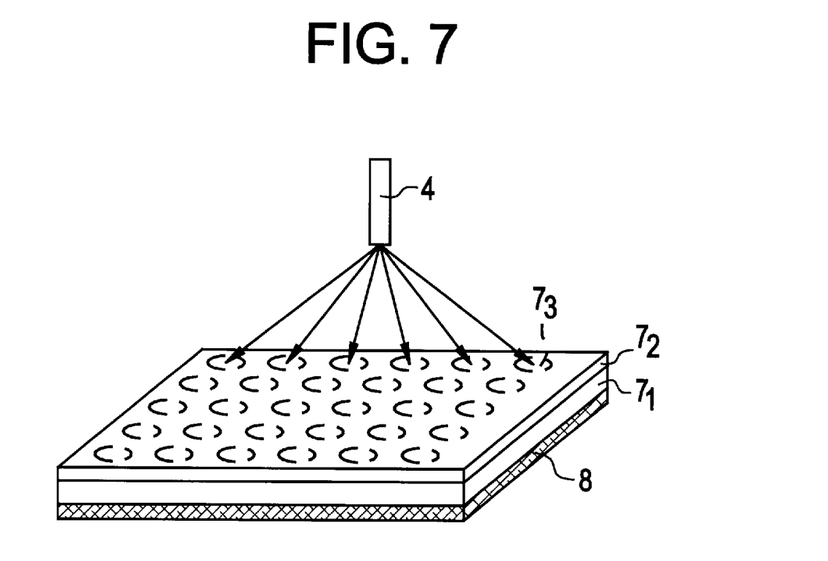
FIG. 7 is a diagram showing the principle of the multisensor structure Sc/Is-$Pr_1$ to $Pr_n$.

The appended FIG. 7 is a diagram showing the principle of the multisensor structure Sc/Is-$Pr_1$ to $Pr_n$. The same reference numbers have been used as in FIG. 1 to denote the illumination means 4, the probes $Pr_1$ to $PR_n$ identified by the reference number 7.3, the layer Is 7.2 and the semiconductor wafer Sc referenced by 7.1. There is also the ohmic contact 8.

INDUSTRIAL APPLICATION

This type of device opens the way to many and various applications in the field of genetics: the detection of viral disorders and genetic disorders, the checking of histocompatibility, the construction of genome maps, the expression or mutation of genes, etc.

The advantage of this device, compared with the other devices used for multiple detection, lies in its simplicity of construction and in the simplicity of the reading mode associated with direct recognition of the hybridization process.

According to another of these aspects, the invention also relates to the affinity sensors, that is to say the measurement structures Sc/Is-Pr and the reference structures Sc/Is, as described above.

The examples which follow will make it possible to better understand the invention and to bring out all its advantages and its alternative forms, both from the standpoint of the method and that of the device.

EXAMPLES

Example 1

MEASUREMENT OF THE OPTOELECTROCHEMICAL IMPEDANCES USING THE DEVICE OF THE INVENTION COMPRISING A STRUCTURE Sc/Is AS BASE ELEMENT OF THE BIOSENSOR 1.1. APPARATUS

The device employed in this example corresponds to that illustrated in FIG. 1.

The structure Sc/Is comprises:
- a semiconductor, having a thickness of 0.03 mm, which is silicon p-doped to a level of approximately $10^{15}$ cm$^{-3}$ with, on the rear face, an Au/Cr layer providing the ohmic contact,
- and an insulator Is, which is silica, having a thickness of 10 nm, obtained by thermal oxidation.

1.2. CONDUCTIVE LIQUID MEDIUM CL: BUFFER SOLUTION, TRIS 1M.

This buffer solution, having a pH of 7.1, is composed of 10 mM Tris-HCl (Sigma) and 50 mM NaCl.

1.3 THE EXPERIMENTAL CONDITIONS ARE AS FOLLOWS:

The frequency of the light modulations is 316 hertz;

The light source is a helium-neon laser emitting illumination at a wavelength 632.8 nm;

The luminous power is 0.6 $\mu$W/cm$^2$.

1.4 RESULTS

Figure 8:
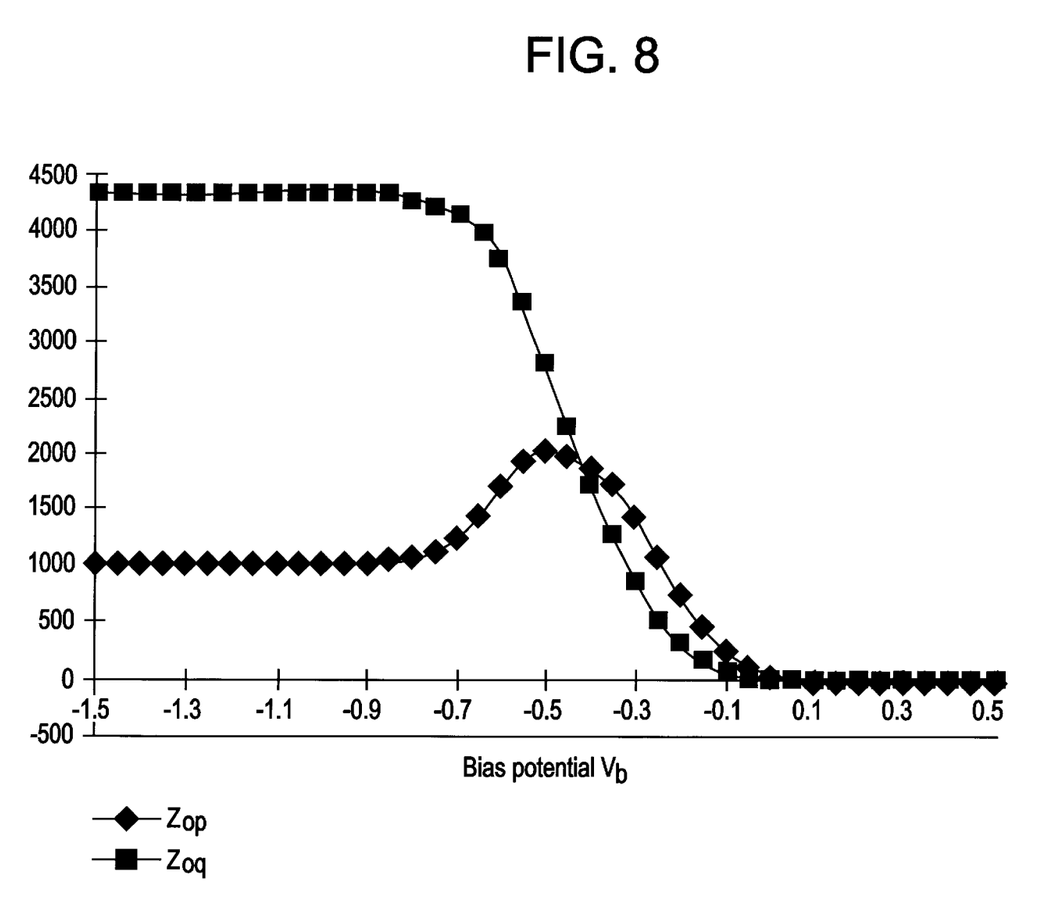
FIG. 8 shows the $Z_{op}$ and $Z_{oq}$=f($V_b$) curves obtained.

The appended FIG. 8 shows the curves of the optoelectrochemical impedance components $Z_{op}$ and $Z_{oq}$ as a function of $V_b$ which are obtained for the structure described above.

In the negative bias range, the quadrature impedance component is due to the capacitance of the space-charge region of the semiconductor, this being directly linked to the doping of the semiconductor. In the positive bias range, the quadrature impedance component is very small since the semiconductor is in an accumulation situation and the capacitance of the space-charge region is very high. In the intermediate bias range, the semiconductor passes successively from the inversion situation to the depletion situation and then to the accumulation situation, as the bias increases.

The in-phase impedance component has a peak in the intermediate range. This peak is due to the presence of interface states lying between the semiconductor and the oxide layer. Thus, the optoelectrochemical impedance components give energy information about the semiconductor and about the surface states of the semiconductor, but give no information about the dielectric layer. However, they do make it possible to determine the flat band potential of the semiconductor. The value of the flat band potential is correlated with the position of the curve of the quadrature impedance component with respect to the potential axis. This is the parameter which allows the surface charge of the structure to be characterized.

Example 2

APPLICATION OF THE IMPEDANCE MEASUREMENTS ACCORDING TO THE EXAMPLE TO THE BIOLOGICAL DETECTION: PN=DNA (OLIGO dT), 1$^{ST}$ MODE OF IMPLEMENTATION, WEAK-ILLUMINATION VERSION 2.1 THE DEVICE

The device used, including the structure Sc/Is and the conductive medium CL, is the same as in Example 1 except that the structure Sc/Is is functionalized by probes Pr consisting of nucleotides cPN, complementary to target species PN contained in CL.

2.2 FUNCTIONALIZATION OF THE SURFACE OF THE INSULATOR Is BY PROBES Pr CONSISTING OF 20-BASE dT OLIGONUCLEOTIDES

After hydroxylating the Si/SO$_2$ surface, a polymeric layer of APTS (aminopropyltriethoxysilane) is deposited. The oligonucleotide strands (dT) are grafted onto the surface by bromination: this method allows the nucleotide to be attached to the APTS without using the sites involved in the hybridization. Finally, the hybridization is obtained after having left the structure in contact with a solution containing poly(dA) strands complementary to those attached to the surface.

2.3 RESULTS

Figure 9:
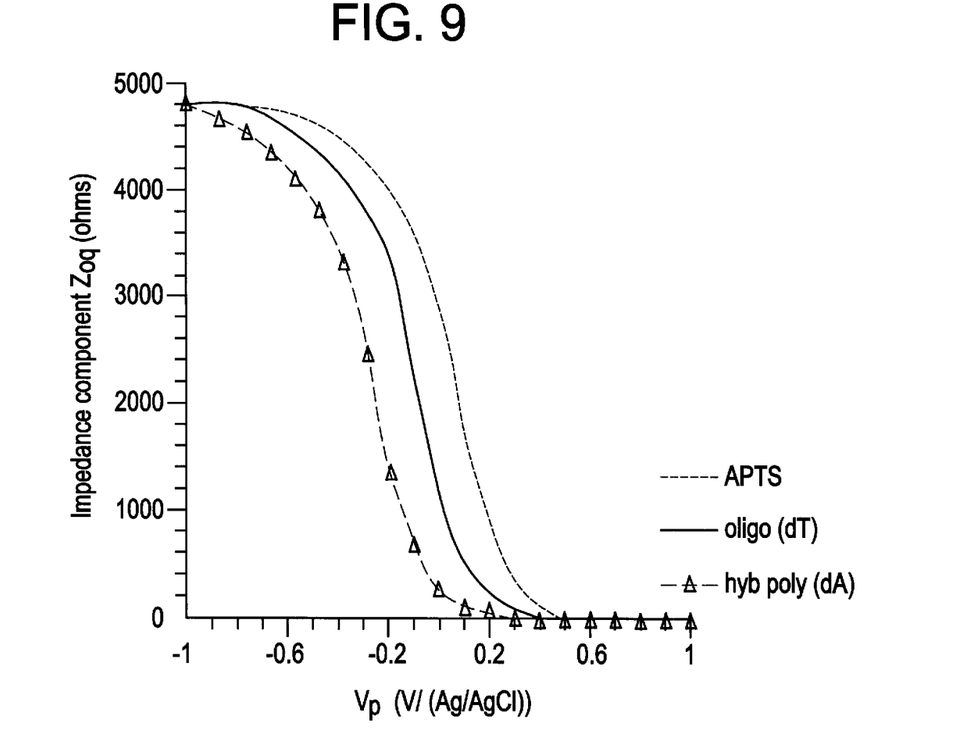
FIG. 9 corresponds to the impedance component curves obtained at each step in the production of a functionalized active structure for recognizing simple DNA strands.

FIG. 9 corresponds to the impedance component curves obtained at each step in the production of a functionalized active structure for recognizing simple DNA strands.

The curves in FIG. 9 show the shift due to the hybridization of the complementary strands cPN/PN of DNA.

Example 3

ANALYSIS OF POLYNUCLEOTIDES (PN) USING THE DEVICE ACCORDING TO THE INVENTION (FIG. 1), 1$^{ST}$ MODE OF IMPLEMENTING THE METHOD, STRONG-ILLUMINATION VERSION

Figure 10:
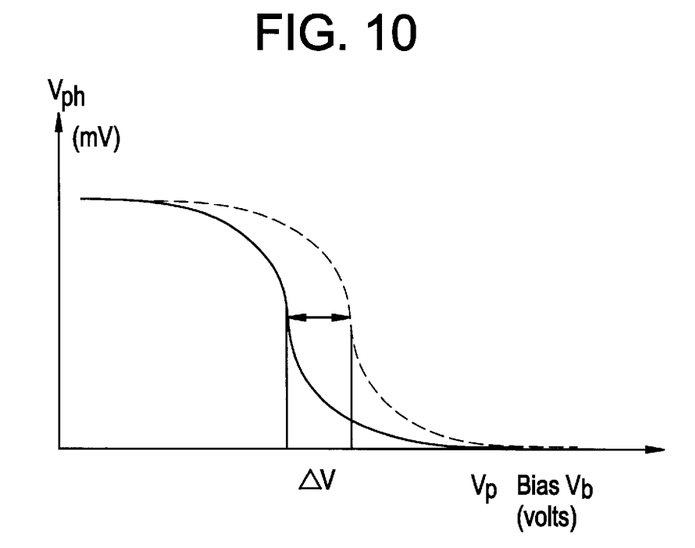
FIG. 10 is a $V_{ph}$=f($V_b$) curve obtained in Example 3 in order to illustrate a first mode of implementing the strong-illumination method.

FIG. 10 represents the GENOPTRODE $V_{ph}=f(V_b)$ curve.

Example 4

ANALYSIS OF POLYNUCLEOTIDES (PN) USING AN ALTERNATIVE VERSION OF THE DEVICE ACCORDING TO THE INVENTION (FIG. 5), IN THE SECOND MODE OF IMPLEMENTING THE METHOD, VERSION (ii)

4.1 THE DEVICE

The device used is that described in FIG. 5. The measurement cell and the affinity sensor are those illustrated in FIG. 2. The modulated light is delivered by means of a light-emitting diode and the luminous power used is 10 mW/cm$^2$.

4.1 EXPERIMENTAL CONDITIONS AND FUNCTIONALIZATION

The conductive liquid CL is an aqueous solution of 10 mM tris(hydromethyl)aminomethane hydrochloride (Sigma) and 50 mM NaCl; the overall solution has a pH of 7.1. The measurement is carried out at room temperature, i.e. 22° C., in the dark.

The structure Sc/Is-Pr is as described in the previous examples. In this example, the probes are cPNs, and more specifically 20-base dT oligonucleotides, which are deposited on the region shown as 7.3 in FIG. 2 using a solution composed of 20 $\mu$l of an aqueous solution of n-bromosuccinimide having a concentration of 0.01M added to 1 ml of a 1M NaHCO$_3$ aqueous solution containing (dT)20 oligonucleotides having a concentration of 1 mg/ml. The structure is left overnight in contact with the solution of the cPNs, then thoroughly rinsed with the liquid CL and then mounted in the measurement cell. This cell is then filled with CL and the measurement system is initialized.

4.3 RESULTS

Figure 11:
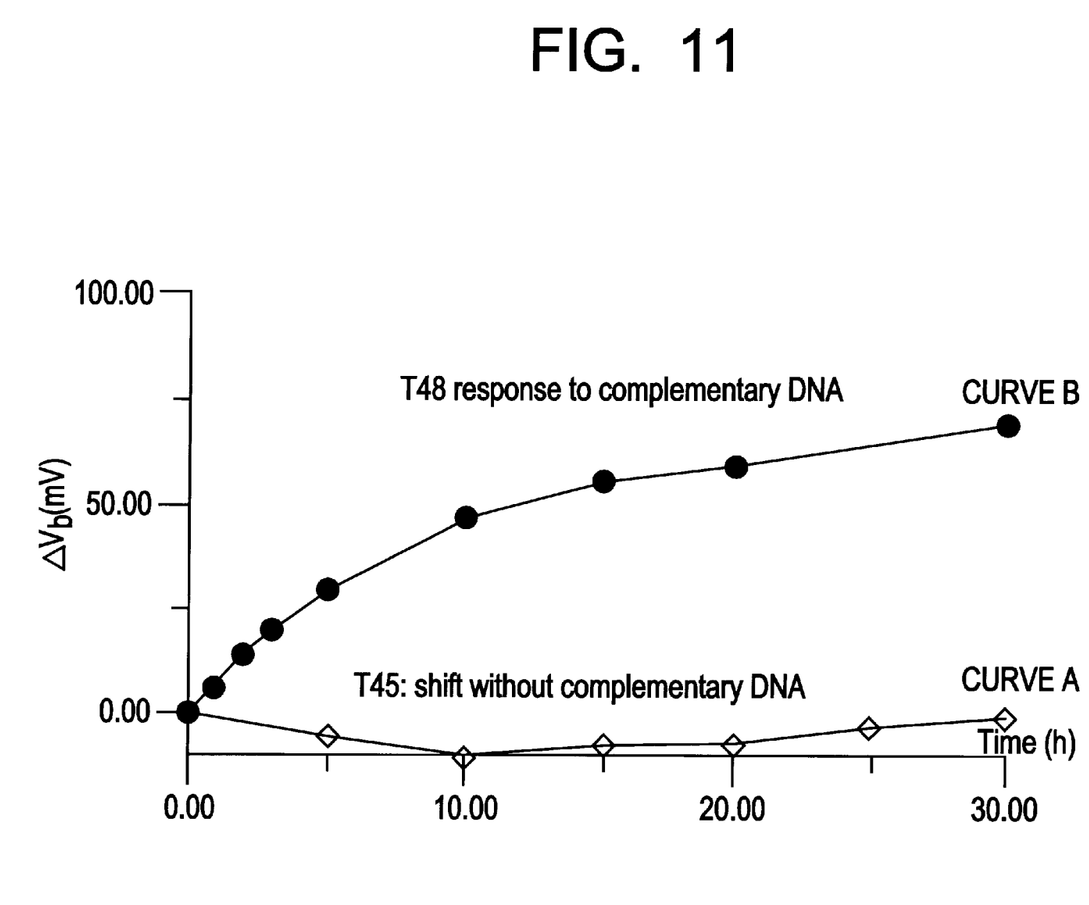
FIG. 11 gives the $\Delta V_b$ response of the functionalized structure for detecting oligonucleotides in Example 4, $2^{nd}$ mode of implementation, version (ii).

FIG. 11 gives the $\Delta V_b$ response over time of the functionalized structure Sc/Is-Pr in which the probes are (dT) oligonucleotides.

Curve A corresponds to the response obtained when the sensor is in contact with a solution CL to which has been added targets (dC polynucleotides having a concentration of 1 µg/ml) which are not complementary to the probes fixed to the sensor.

Curve B corresponds to the response obtained when the sensor is in contact with a solution CL to which has been added targets (dA polynucleotides having a concentration of 1 µg/ml) which are complementary to the probes fixed to the sensor.

What is claimed is:

1. A apparatus for identifying and/or quantifying a charged biological substance in a conductive liquid medium, comprising:
   a chamber for the conductive liquid medium;
   an affinity sensor disposed in said chamber; said affinity sensor comprising
      a semiconductor having an upper and a lower surface; said semiconductor having an ohmic contact disposed on its lower surface;
      an insulator layer disposed on the upper surface of said semiconductor;
      a plurality of probes in contact with said conductive liquid medium; said
      plurality of probes being disposed on the surface of said insulator layer; said
      plurality of probes comprising a recognition biological substance which is able to specifically hybridize with a charged biological substance present in the conductive liquid medium, whereby specific pairings of charged biological substances with their complementary recognition biological substances are formed; said specific pairings modifying the surface electric charge of the affinity sensor;
   means for biasing the semiconductor with respect to the conductive liquid medium;
   means for illuminating the semiconductor;
   means for measuring a photopotential $V_{ph}$ at the terminals of the affinity sensor;
   means for converting the detected signals into $V_{fb}$ variations which are induced by a charge-effect phenomenon associated with said pairings modifying the surface electric charge of the affinity sensor; and
   means for calculating and interpreting the $\Delta V_{fb}$ variations in terms of the identification and/or quantitative determination of the charged biological substances.

2. An apparatus according to claim 1, wherein said semiconductor is a silicon semiconductor.

3. An apparatus according to claim 1, wherein said insulator layer is a silica or silicon nitride insulator layer.

4. An apparatus according to claim 1, wherein said recognition biological substance is a polynucleotide.

5. An apparatus according to claim 1, further comprising an auxiliary electrode.

6. An apparatus according to claim 5, wherein said auxiliary electrode is disposed on the insulator layer.

7. An apparatus according to claim 1, comprising a means. for evaluating the variation in $V_{ph}$ signal with respect to a reference U, and a means for correcting the variation in $V_{ph}$ signal by acting on the biasing means.

8. An apparatus according to claim 1, further comprising a reference structure not functionalized by a probe or probes.

9. An apparatus according to claim 1, wherein the probes are of different types, and wherein probes of the same type are grouped in the same region on the insulator layer to allow separate and/or successive illumination.

10. An affinity sensor according to claim 1.

11. A method of identifying and/or quantifying a charged biological substance in a conductive liquid medium using an apparatus comprising:
   a chamber for the conductive liquid medium;
   a affinity sensor disposed in said chamber; said affinity sensor comprising
      a semiconductor having an upper and a lower surface; said semiconductor having an ohmic contact disposed on its lower surface;
      an insulator layer disposed on the upper surface of said semiconductor;
      a plurality of probes in contact with said conductive liquid medium; said
      plurality of probes being disposed on the surface of said insulator layer; said
      plurality of probes comprising a recognition biological substance which is able to specifically hybridize with a charged biological substance present in the conductive liquid medium, whereby specific pairings of charged biological substances with their complementary recognition biological substances are formed;
   means for biasing the semiconductor with respect to the conductive liquid medium;
   means for illuminating the semiconductor;
   means for measuring a photopotential $V_{ph}$ at the terminals of the affinity sensor;
   means for converting the detected signals into $V_{fb}$ variations which are induced by a charge-effect phenomenon associated with said pairings modifying the surface electric charge of the affinity sensor; and
   means for calculating and interpreting the $\Delta V_{fb}$ variations in terms of the identification and/or quantitative determination of the charged biological substances;
   wherein the method comprises
      providing an unlabeled recognition biological substance as a probe;
      contacting the charged biological substance with the unlabeled recognition biological substance, whereby specific pairings of charged biological substances with their complementary recognition biological substances are formed; said specific pairings modifying the surface electric charge of the affinity sensor;
      biasing the semiconductor to ensure that the Fermi level corresponds approximately to, or exceeds, the intrinsic Fermi level at the surface of the semiconductor;
      exposing the semiconductor to periodic illumination comprising photons having an energy greater than or equal to the band gap energy of the semiconductor;
      measuring the photopotential $V_{ph}$ at the terminals of the affinity sensor;
      determining the complex impedance of the affinity sensor from the photopotential $V_{ph}$, determining the variations $\Delta V_{fb}$ of the semiconductor which are induced by a charge-effect phenomenon associated with said specific pairings of the charged biological substances with their complementary recognition biological substances; to the exclusion:
         (i) of the variations resulting from possible charge and/or charge-transfer effects caused by enzyme-catalyzed chemical reactions in which some of the substances to be detected are consumed; and
         (ii) and of the variations in the photoresponse which are associated with the appearance in the conductive medium of at least one tracer product capable of being revealed through pH variations or redox potential variations and/or through radiation-absorbing or radiation emitting labels; and identifying and/or quantifying the charged biological substances in the conductive liquid medium by interpreting the received signals.

12. A method according to claim 11, wherein the specific pairings of charged biological substance comprise an enzyme-substrate complex.

13. A method according to claim 11, wherein the specific pairings of charged biological substance comprise an immunological complex.

14. A method according to claim 11, wherein the charged biological substance is a polynucleotide and the recognition biological substance is a polynucleotide.

15. A method according to claim 11, wherein the semiconductor is biased by imposing a bias voltage $V_b$ by sweeping between a negative limiting voltage and a positive limiting voltage; and wherein $\Delta V_{fb}$ is measured by detecting the photopotential $V_{ph}$ at the terminals of the semiconductor; optionally calculating the in-phase component $Z_{op}$ and/or the quadrature component $Z_{oq}$ of the optoelectrochemical impedance for each value of $V_b$; constructing $Z_{op}$ and/or $Z_{oq}$ and/or $V_{ph}$ curve as a function of $V_b$; and monitoring the shift in the curve parallel to the x-axis, said shift corresponding to the desired variations in $V_{fb}$.

16. A method according to claim 11, wherein the periodic illumination is approximately sinusoidal weak illumination.

17. A method according to claim 11, wherein the periodic illumination is strong illumination.

18. A method according to claim 11, wherein the $V_{fb}$ variations are obtained by detecting $V_{ph}$ and constructing a $V_{ph}=f(V_b)$ curve; and monitoring a shift in the curve parallel to the x-axis, said shift corresponding to the desired $\Delta V_{fb}$ values.

19. A method according to claim 11, wherein the Fermi level of the semiconductor is set approximately to the intrinsic Fermi level at the surface of the semiconductor by imposing a bias voltage $V_b$ corresponding approximately to the abscissa of the point of inflection of the $V_{ph}=f(V_b)$ or $Z_{oq}=f(V_b)$ curve, wherein the ordinate of the point of inflection corresponds approximately to $V_{ph}$, ½ max and $Z_{oq}$, ½ max; and wherein the variations in $\Delta V_{fb}$ in $V_{fb}$ are obtained (i) by measuring the change in $V_{ph}$ and/or $Z_{oq}$; and/or (ii) by taking into account the variations in the bias voltage $\Delta V_b$ made necessary to keep $V_{ph}$, ½max or $Z_{oq}$, ½ max constant, this $\Delta V_b$ adjustment being the reflection of $\Delta V_{fb}$.

20. A method according to claim 11, which comprises detecting the photopotential signal $V_{ph}$; optionally amplifying the signal $V_{ph}$; optionally rectifying the signal to give a DC signal $V'_{ph}$; comparing the DC signal $V'_{ph}$ with a reference signal U corresponding approximately to the value of $V'_{ph}$, ½ max; obtaining the difference between $V'_{ph}$ and U, namely $\Delta(V'_{ph}-U)$; optionally amplifying $\Delta(V'_{ph}-U)$; applying the optionally amplified $\Delta(V'_{ph}-U)$ between the semiconductor and the conductive liquid medium as a complement of $V_b$; and recording $\Delta(V'_{ph}-U)$.

21. A method according to claim 11, wherein the wavelength $\lambda$ of the illumination is greater than or equal to a threshold $\lambda_0$, where $$\lambda_0 = \frac{1240}{E} \text{ nm.}$$

22. A method according to claim 21, wherein the wavelength is between 100 and 3000 nm.

23. A method according to claim 11, further comprising using a reference structure comprising a semiconductor and an insulator layer wherein said insulator layer is not functionalized by a probe; and monitoring the difference between the $V_{bp}$ variations measured by the two sensors, and the variation in this difference.

24. A method according to claim 11, wherein the insulator layer is functionalized by different types of polynucleotides as recognition biological substance, and wherein the conductive liquid medium comprises different types of polynucleotides as charged biological substance; and wherein said probes of the same type are grouped in the same region on the insulator layer to allow separate and/or successive illumination.

25. A method according to claim 11, wherein the charged biological substance is selected from the group consisting of nucleotides, oligonucleotides, polynucleotides, nucleic acids and mixtures thereof.

26. A method according to claim 24, wherein at least one affinity sensor is used without a compartment at the surface of the affinity sensor.

* * * * *